US00PP36706P3

(12) United States Plant Patent
Yoshida et al.

(10) Patent No.: US PP36,706 P3
(45) Date of Patent: May 27, 2025

(54) CHERRY TREE NAMED 'Himari'

(50) Latin Name: ***Prunus avium* (L.) L.**
Varietal Denomination: Himari

(71) Applicant: Local Independent Administrative Agency Hokkaido Research Organization, Hokkaido (JP)

(72) Inventors: Masayuki Yoshida, Hokkaido (JP); Mitsunobu Ikenaga, Hokkaido (JP); Tetsuya Inoue, Sapporo (JP); Tetsushi Uchida, Hokkaido (JP); Takuya Hirama, Hokkaido (JP); Yutaka Inagawa, Hokkaido (JP); Hiroshi Muramatsu, Hokkaido (JP)

(73) Assignee: Local Independent Administrative Agency Hokkaido Research Organization, Hokkaido (JP)

( * ) Notice: Subject to any disclaimer, the term of this patent is extended or adjusted under 35 U.S.C. 154(b) by 0 days.

(21) Appl. No.: 18/445,020

(22) Filed: Mar. 3, 2023

(65) Prior Publication Data

US 2023/0301219 P1 Sep. 21, 2023

(30) Foreign Application Priority Data

Mar. 16, 2022 (JP) ..... 36084

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

*Primary Examiner* — Kent L Bell
(74) *Attorney, Agent, or Firm* — Kilpatrick Townsend & Stockton LLP

(57) ABSTRACT

'Himari' is new cherry tree variety having excellent fruit-setting property and cold hardiness, a large fruit size, and large productivity. 'Himari' can be distinguished from similar varieties by its dark red color, medium to firm fruit, small stone size and large fruit size.

7 Drawing Sheets

Genus and species: The variety of cherry tree of this invention is botanically identified as *Prunus avium* (L.) L.

Variety denomination: The variety denomination is 'Himari'.

CROSS REFERENCE TO RELATED APPLICATIONS

This application claims priority to Japanese Plant Variety Protection Application No. 36084, filed Mar. 16, 2022.

BACKGROUND OF THE INVENTION

The cherry breeding experiment that led to the selection of this variety started in Hokkaido, Japan in 1990 and has been carried out since 1992 in order to obtain a cherry variety having good eating quality, large size, good coloration, and cross compatibility with 'Sato Nishiki' (unpatented).

Cherry tree 'Himari' was created in 2002 by the artificial crossing of 'Nanyo' (unpatented), which was obtained from a cross of 'Napoleon' (unpatented) and an unknown variety, having a large size and excellent eating quality bred in Yamagata Prefecture, Japan, as a seed parent; and 'Benitemari' (unpatented), which was obtained from a cross of 'Bic' and 'Sato Nishiki', having a large size and excellent eating quality and coloration, also bred in Yamagata Prefecture, Japan, as a pollen parent. The cross between 'Nanyo' and 'Benitemari' took place in Hokkaido, Japan. In 2002, 467 seeds obtained by crossing were sowed and 264 individuals were obtained as of December 2002. After overwintering, 27 individuals surviving in 2003 were planted and investigated. Individual '60-18' (also referred to as 'HC10' for further testing and later provided the variety designation of 'Himari') having excellent fruit-setting property and cold hardiness, a large fruit size, and large productivity was selected in 2013. This individual has excellent appearance and eating quality and had been subjected to a fruit regional adaptability test since 2014 in Yoichi town, Japan, Fukagawa City, Japan, and further characterized for development since 2015 in Mashike Town, Japan. 'Himari' can be distinguished from its parents and other cherry tree varieties based on the collective distinctive combination of characteristics. The S gene of 'Himari' is $S_1S_3$ whereas the S gene of 'Benitemari' is $S_1S_6$. The flowering period for 'Himari' is 2 days later than 'Sato Nishiki', which is 1-2 days later than 'Benitemari'. The ripening period in Hokkaido, Japan, for 'Himari' is mid-late July in comparison to the ripening period for 'Benitemari', which is late July. 'Benitemari' has short, heart-shaped oblate round fruit whereas 'Himari' has kidney-shaped fruit. Initial asexual reproduction by grafting took place in Naganuma Town, Hokkaido Prefecture, Japan. Subsequent asexual propagation by grafting was conducted in Yamagata Prefecture, Japan, confirmed that the new variety is stable and the progeny remain true to type.

SUMMARY OF INVENTION

'Himari' is a late-maturing tree which is harvested in mid-to late-July in Hokkaido. Compared to 'Nanyo', 'Himari' has a large size, good skin coloration, medium to firm fruit firmness, and excellent eating quality. The S genotype is $S_1S_3$, which is cross-compatible with most cultivated varieties including 'Sato Nishiki'. 'Himari' can thus improve the pollination environment of orchards and contribute to ensuring the fruiting of other varieties.

'Himari' can be distinguished from similar varieties 'Nanyo' and 'Sato Nishiki' based on the color of skin, fruit firmness, and the size of the fruit and stone. The skin color of 'Himari' is "dark red" (strong red 46A), which is darker compared to the "light red" skin color of 'Nanyo' and "red" skin color of 'Sato Nishiki'. The fruit firmness of 'Himari' is medium to firm compared to soft to medium firmness for 'Nanyo' and medium firmness for 'Sato Nishiki'. The stone weight of 'Himari' is small (0.32 g) compared to the stone of 'Nanyo', which is small to medium (0.35 g). The fruit weight of 'Himari' is very large (10.7 g) compared to medium-sized fruit of 'Sato Nihsiki' (7.6 g).

BRIEF DESCRIPTION OF THE PHOTOGRAPHS

The colors in the photographs are depicted as nearly true as is reasonably possible to obtain in color reproductions of this type.

DETAILED DESCRIPTION

Figure 1:
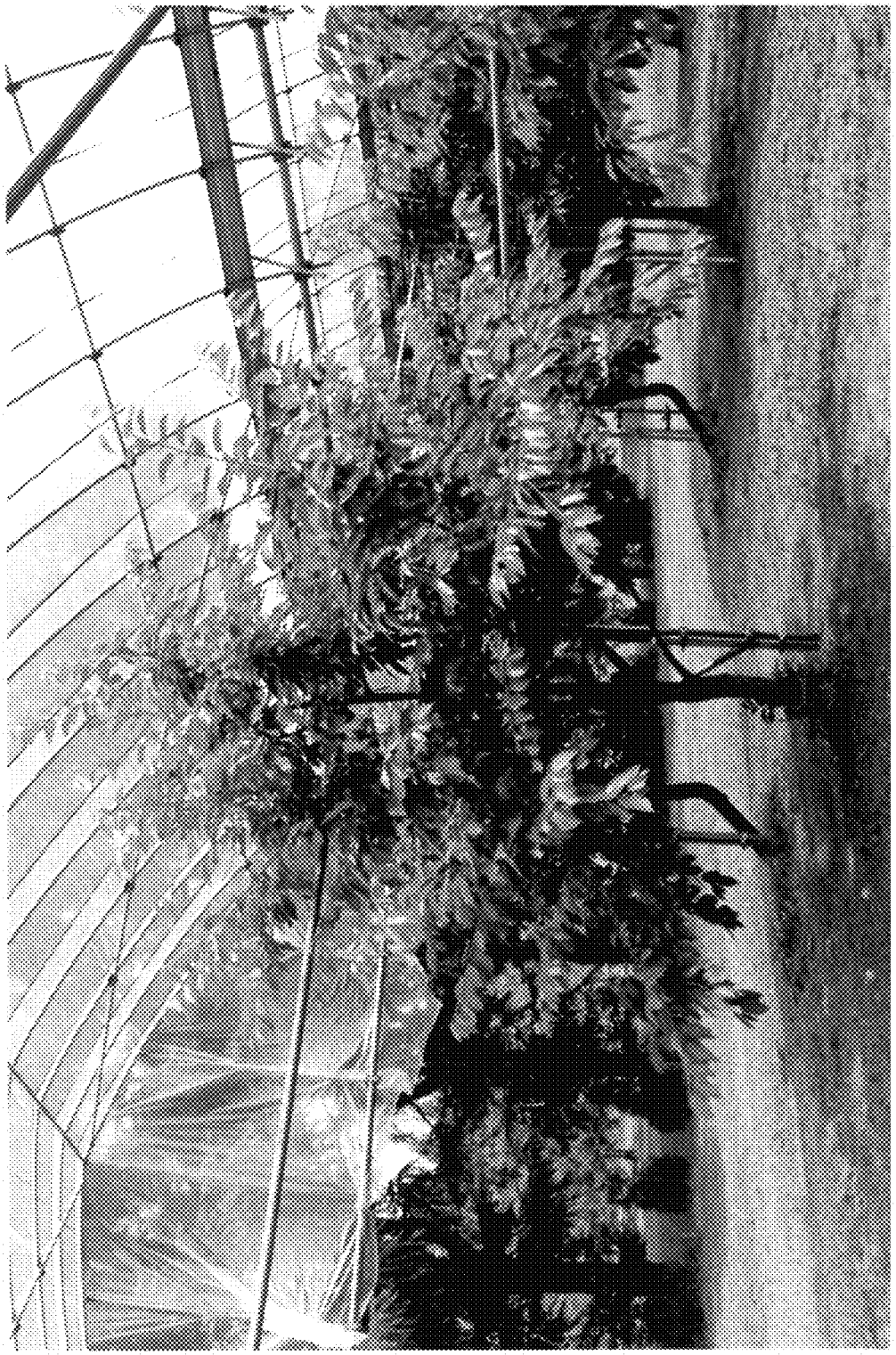
FIG. 1 illustrates a typical 9-year old 'Himari' tree (Naganuma-cho, Yubari-gun, Hokkaido) in July 2021.
Figure 2:
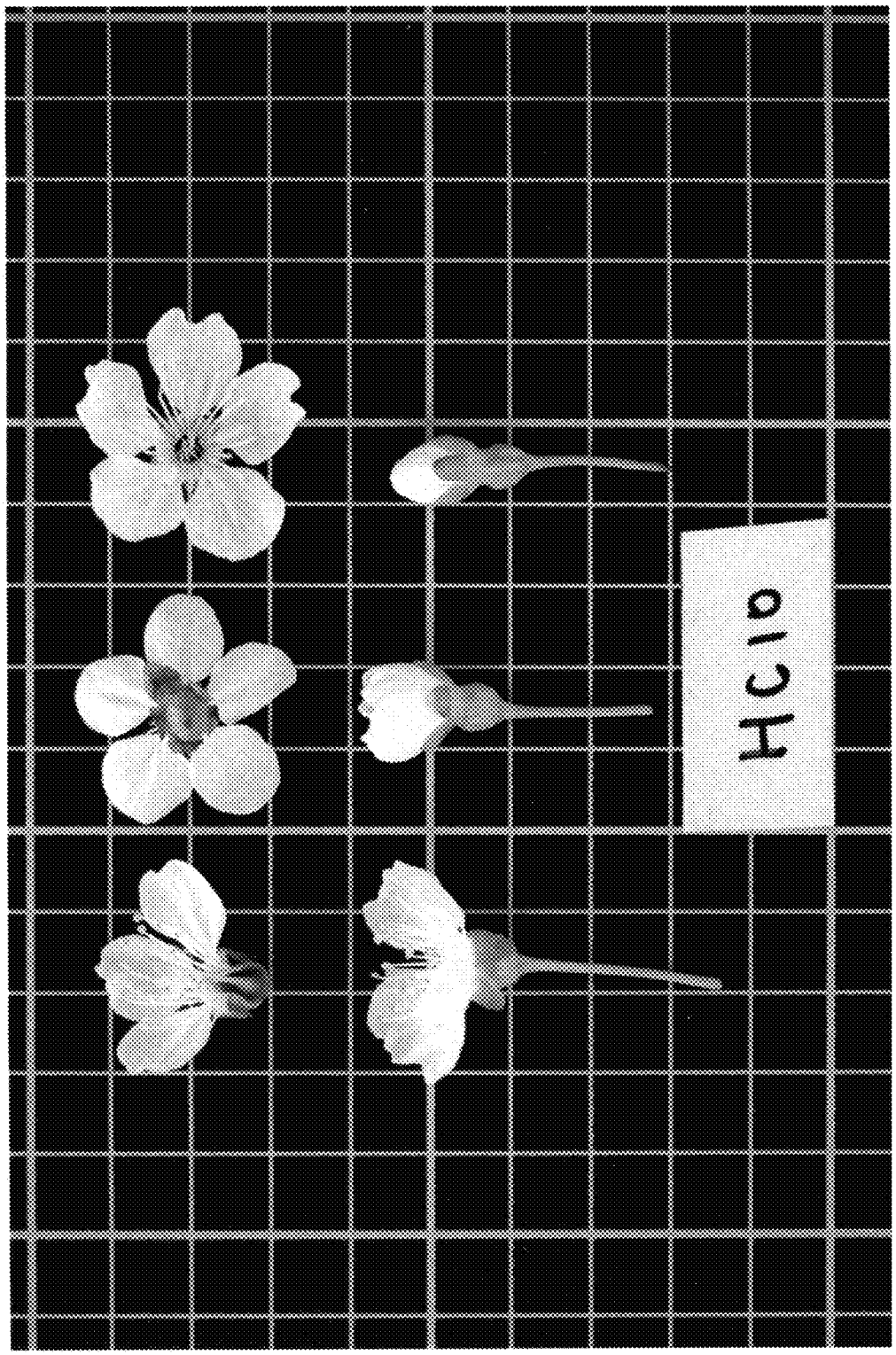
FIG. 2 illustrates flowers of 'Himari'
Figure 3:
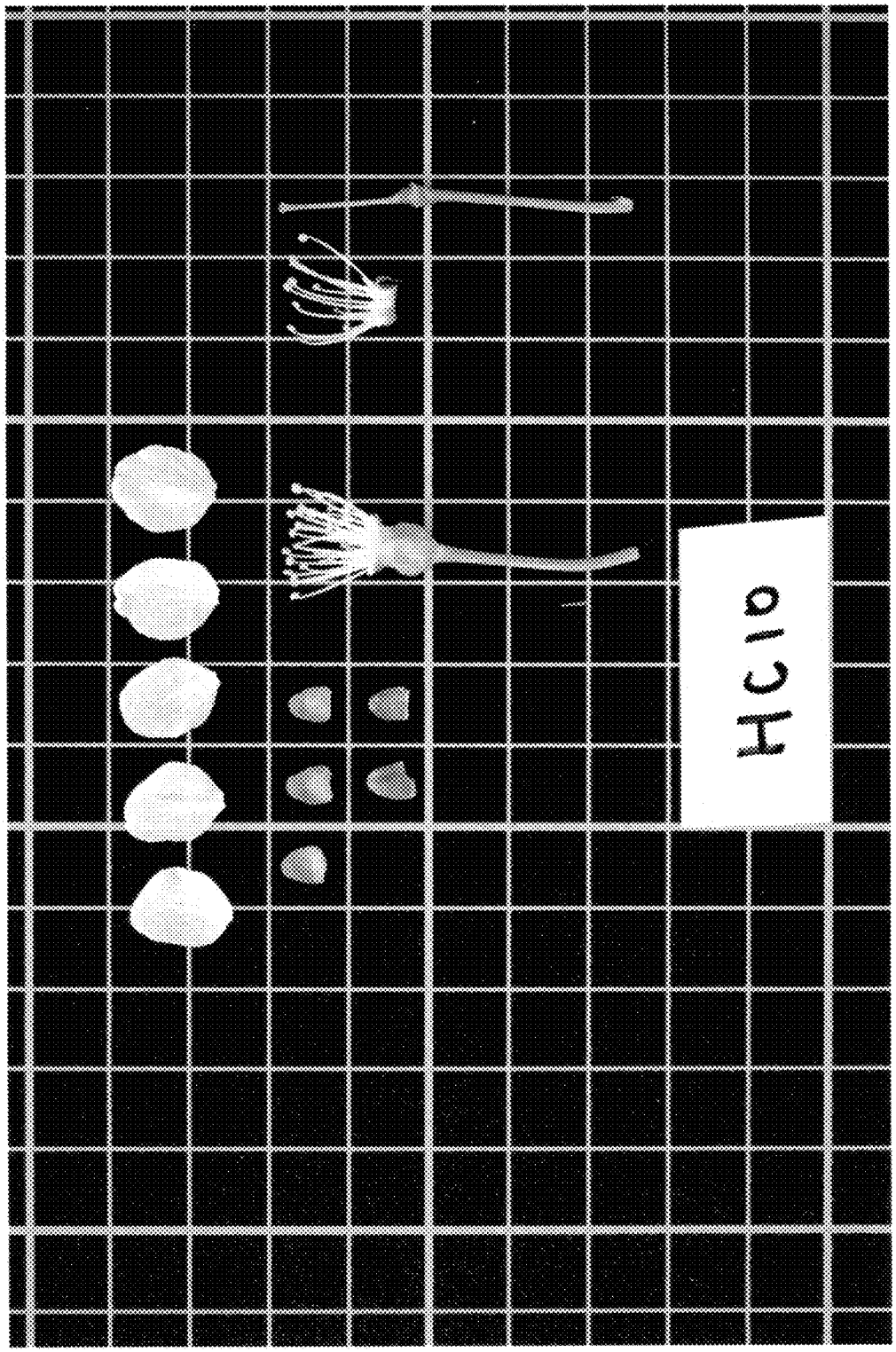
FIG. 3 illustrates parts of 'Himari' flowers.
Figure 4:
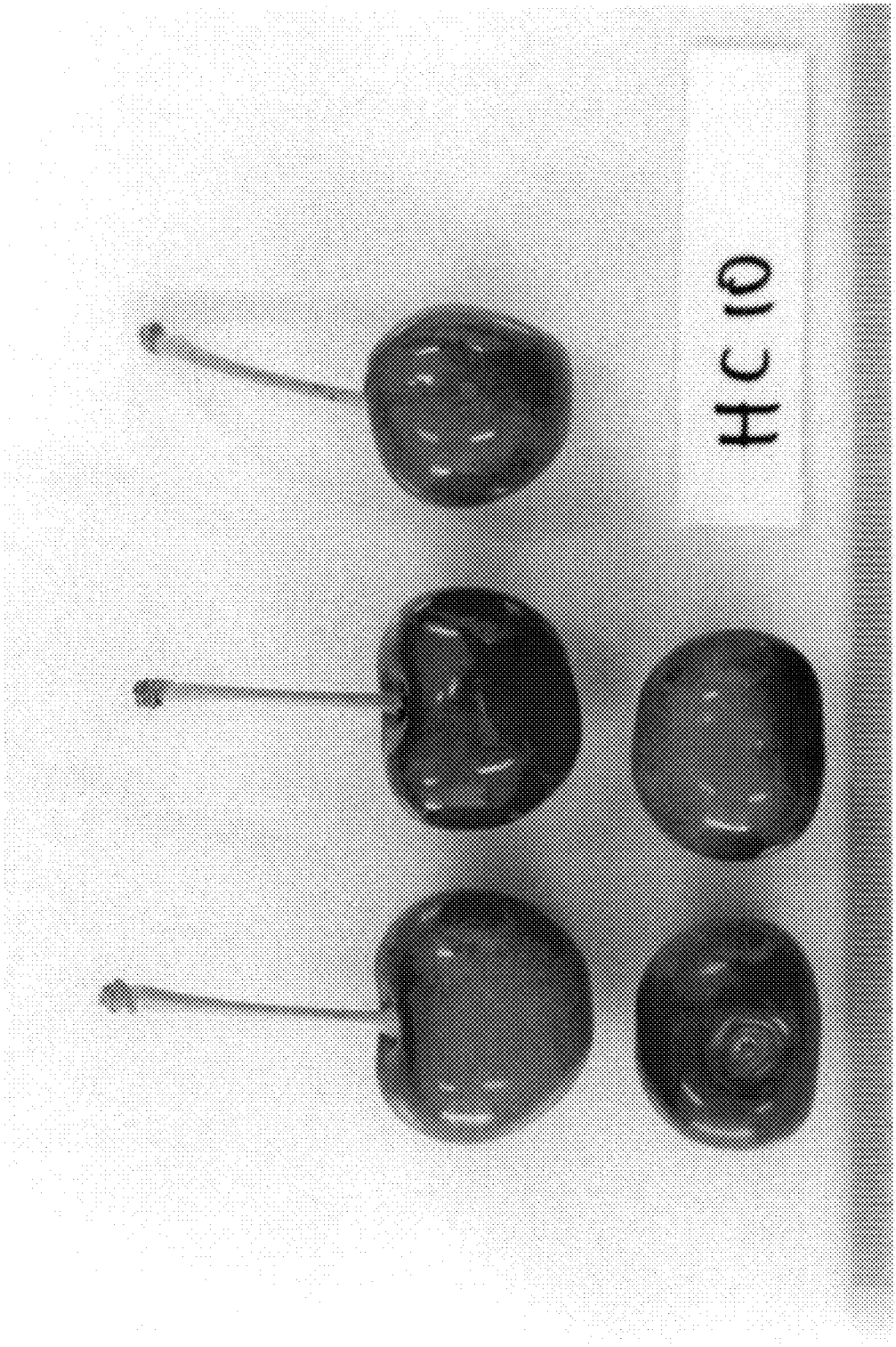
FIG. 4 illustrates 'Himari' fruit.
Figure 5:
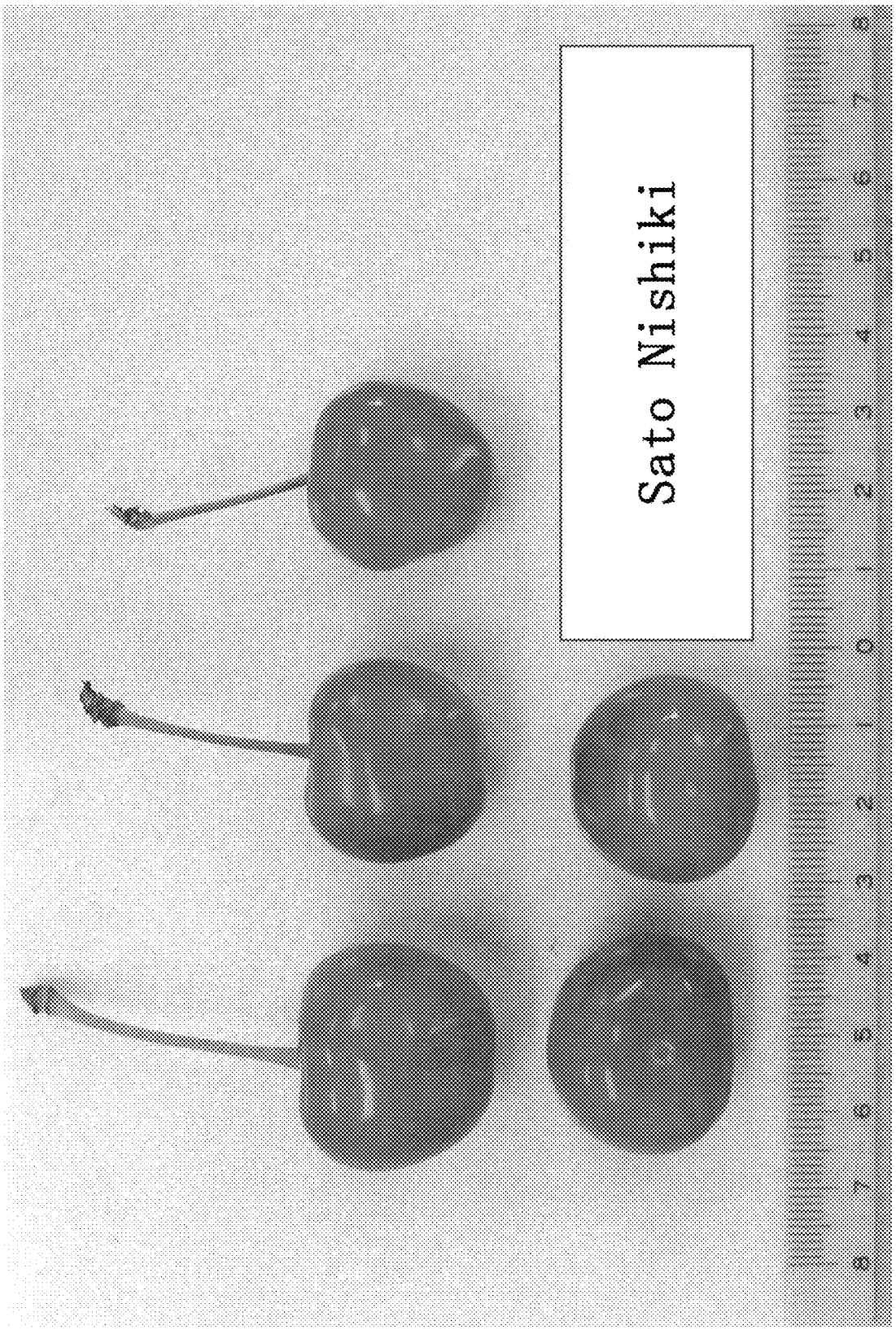
FIG. 5 depicts fruit of comparison variety 'Sato Nishiki'.
Figure 6:
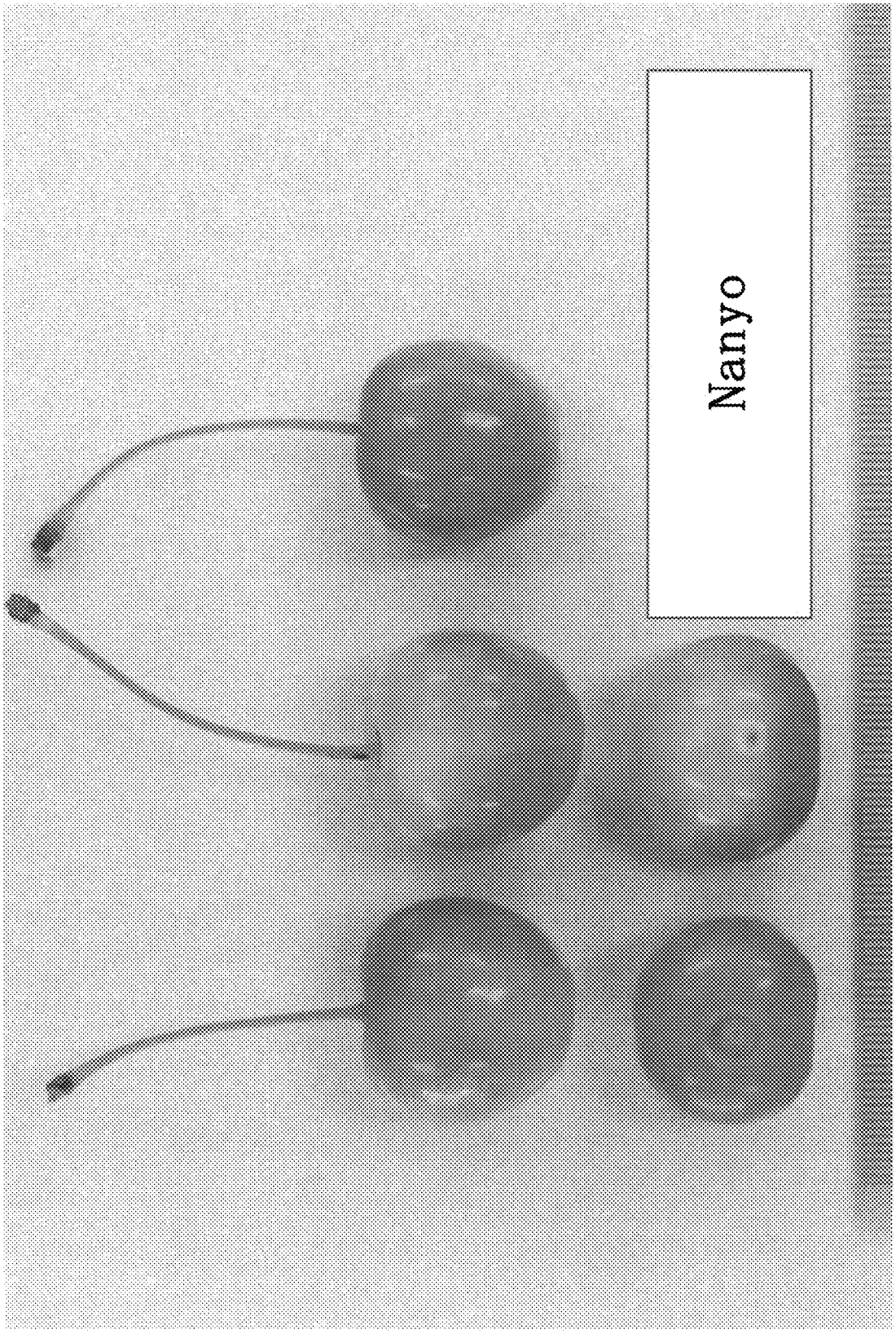
FIG. 6 depicts fruit of comparison variety 'Nanyo'.
Figure 7:
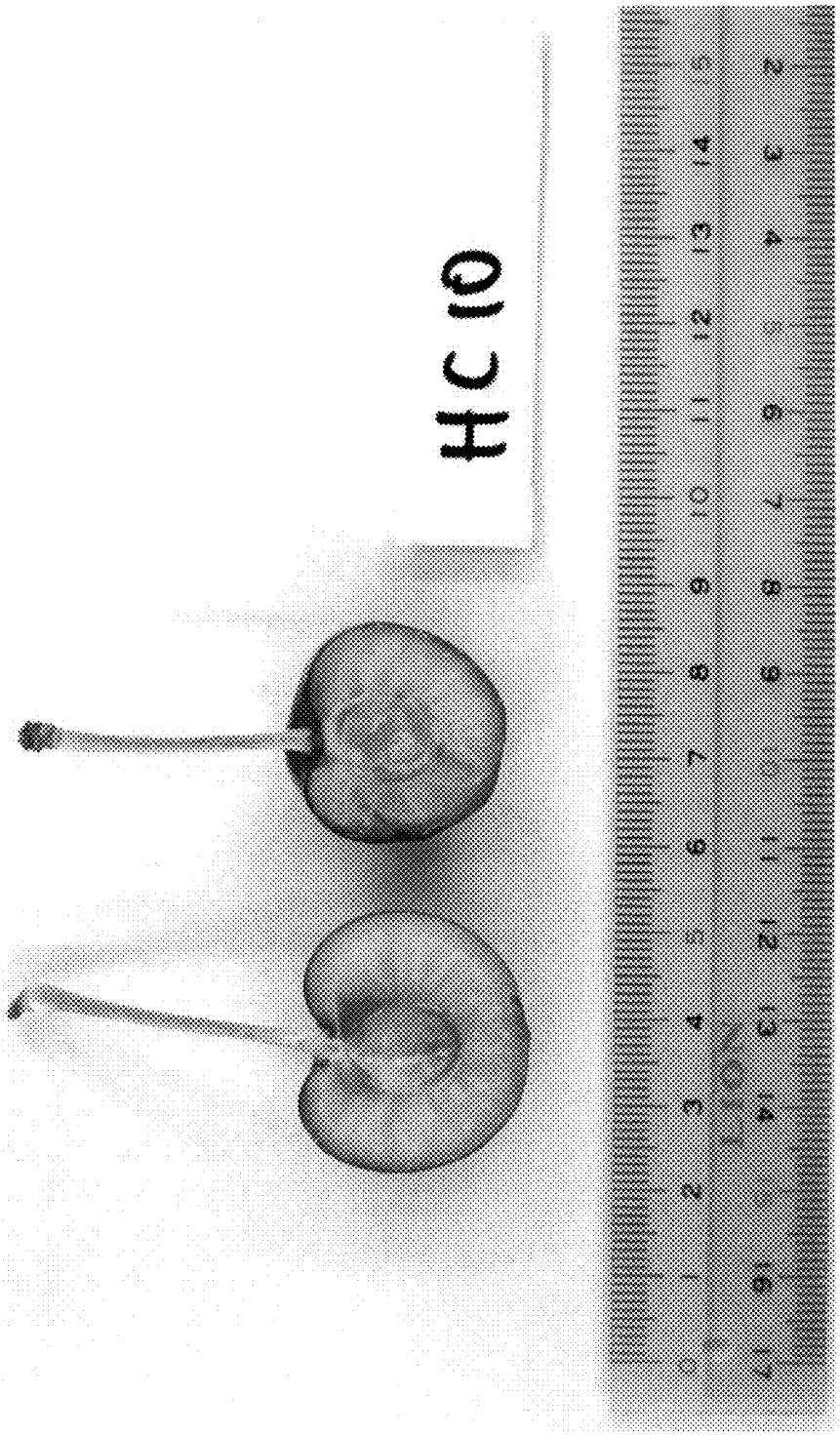
FIG. 7 depicts 'Himari' fruit in cross-section.

The following is a description of 'Himari' trees and fruit that were grown in Hokkaido, Japan. For purposes of this description, 'Himari' is referred to by its earlier designation 'HC10'. The data presented in Table 1 is based on the Characteristic Table for the Japanese Plant Variety Protection application corresponding to UPOV guidelines. Data from additional trials is also provided in this section.

Color designations are from The Royal Horticultural Society Colour Chart, Sixth Edition, issued 2015.

Morphological Characteristics

The tree vigor is "medium to strong", while "strong" for 'Sato Nishiki' and "medium to strong" for 'Nanyo'. The tree habit is "spreading", while "semi-upright" for 'Sato Nishiki' and 'Nanyo'. Tree branching is "weak to medium", while "medium" for 'Sato Nishiki' and 'Nanyo'. The bouquet spur is "medium", which is weaker than "strong" for 'Sato Nishiki' and "medium to strong" for 'Benishuho' and stronger than "weak" for 'Nanyo'.

Ecological Characteristics

The beginning of blooming is "very late", which is slightly later than "late" for 'Sato Nishiki' and equivalent to 'Nanyo'. The beginning of fruit ripening for 'Sato Nishiki' is late June, which is equivalent to the beginning of fruit ripening for 'Nanyo'. The beginning of fruit ripening for 'Himari' is mid to late July.

Fruit Characteristics

The fruit size for 'Himari' is "very large", while "medium" for 'Sato Nishiki' and "very large" for 'Nanyo'. The fruit shape for 'Himari' is "reniform", while "elliptic" for 'Nanyo' and "reniform" for 'Sato Nishiki' and 'Benishuho'. The fruit pistil end is "depressed", while "flat" for 'Nanyo' and "depressed" for 'Sato Nishiki'. The skin color is "dark red" (RHS strong red 46A), which is darker than "the light red skin color for 'Nanyo' and "red" skin color for 'Sato Nishiki'. The skin coloration is "medium to strong", which is slightly stronger than "weak to medium" for 'Nanyo' and equivalent to 'Sato Nishiki'. The skin thickness is "thick", which is thicker than "medium" for 'Sato Nishiki' and "medium to thick" for 'Nanyo' and equivalent to 'Benishuho'. The fruit firmness is "medium to firm", which is firmer than "medium" for 'Sato Nishiki' and "soft to medium" for 'Nanyo' and softer than "firm" for 'Benishuho'. The fruit acidity is "low", which is equivalent to 'Sato Nishiki', 'Nanyo', and 'Benishuho'. The fruit sweetness is "medium to high", which is higher than "medium" for 'Sato Nishiki' and 'Nanyo' and lower than "high" for 'Benishuho'. The fruit juiciness is "strong", which is equivalent to 'Sato Nishiki' and 'Nanyo'. The stone size is "small", which is smaller than 'Sato Nishiki' and 'Nanyo'. The ratio of weight of fruit to weight of stone is "large", while "small" for 'Sato Nishiki' and "medium" for 'Nanyo'.

Illustrative Test Results in Comparison Testing

Table 1 provides comparative results from analysis of characteristics of 'HC10' compared to 'Nanyo', 'Benishuho' and 'Sato Nishiki' performed from 2019 to 2021 in Hokkaido, Japan.

TABLE 1

Comparison of plant characteristics performed from 2019 to 2021 in Hokkaido Japan.

| | 'HC10' | | 'Sato Nishiki' (standard) | |
|---|---|---|---|---|
| Characteristics | State | Grade | State | Grade |
| Tree vigor | medium to strong | 6 | strong | 7 |
| Tree habit | spreading | 3 | semi upright | 2 |
| Tree branching | weak to medium | 4 | medium | 5 |
| Young shoot: anthocyanin coloration of apex | weak to medium | 4 | weak | 3 |
| Young shoot: pubescence of apex | weak | 3 | medium | 5 |
| Leaf blade length | medium | 5 | medium | 5 |
| Bouquet spurs | medium | — | strong | — |
| Time of beginning of flowering | very late | 9 | late | 7 |
| Time of beginning of fruit ripening | late | 7 | medium | 5 |
| Fruit size | very large | 9 | medium | 5 |
| Fruit shape | reniform | 2 | reniform | 2 |
| Fruit pistil end | depressed | 3 | depressed | 3 |
| Fruit suture | strongly conspicuous | 3 | weakly conspicuous | 2 |
| Color of skin | Dark Red 46A | 7 | | |
| Coloration of skin | medium to strong | — | medium to strong | — |

TABLE 1-continued

| Comparison of plant characteristics performed from 2019 to 2021 in Hokkaido Japan. | | | | |
|---|---|---|---|---|
| Thickness of skin | thick | 7 | medium | 5 |
| Color of flesh | Light Yellow 14D | 1 | | |
| Fruit firmness | medium to firm | 6 | medium | 5 |
| Fruit acidity | low | 1 | low | 1 |
| Fruit sweetness | medium to high | 6 | medium | 5 |
| Fruit juiciness | strong | 7 | strong | 7 |
| Stone size | small | 3 | medium | 5 |
| Stone shape in ventral view | broad elliptic | 2 | medium elliptic | 1 |
| Ratio weight of fruit/weight of stone | large | 7 | small | 3 |

| | 'Nanyo' (control) | | 'Benishuho' (comparison) | |
|---|---|---|---|---|
| Characteristics | State | Grade | State | Grade |
| Tree vigor | strong to very strong | 8 | medium to strong | 6 |
| Tree habit | semi upright | 2 | spreading | 3 |
| Tree branching | medium | 5 | weak to medium | 4 |
| Young shoot: anthocyanin coloration of apex | weak | 3 | medium | 5 |
| Young shoot: pubescence of apex | weak | 3 | medium to strong | 6 |
| Leaf blade length | long | 7 | short to medium | 1 |
| Bouquet spurs | weak | — | medium to strong | — |
| Time of beginning of flowering | very late | 9 | medium | 5 |
| Time of beginning of fruit ripening | late | 7 | medium to late | 6 |
| Fruit size | very large | 9 | medium | 5 |
| Fruit shape | elliptic | 5 | reniform | 2 |
| Fruit pistil end | flat | 2 | depressed | 3 |
| Fruit suture | strongly conspicuous | 3 | strongly conspicuous | 3 |
| Color of skin | | | | 5 |
| Coloration of skin | weak to medium | — | medium | — |
| Thickness of skin | medium to thick | 6 | thick | 7 |
| Color of flesh | | | | 2 |
| Fruit firmness | soft to medium | 4 | firm | 7 |
| Fruit acidity | low | 1 | low | 1 |
| Fruit sweetness | medium | 5 | high | 7 |
| Fruit juiciness | strong | 7 | medium | 5 |
| Stone size | small to medium | 4 | medium | 5 |
| Stone shape in ventral view | medium elliptic | 1 | circular | 3 |
| Ratio weight of fruit/weight of stone | medium | 5 | small to medium | 4 |

The trunk texture of 'Himari' is medium shaggy. Roughness increases with the age of the tree. The color of the trunk is Greyish Red 178A.

'Himari' branches have a length of 56.8 cm and diameter of 20.5 mm. The texture of new growth is relatively smooth. Mature growth has a medium rough texture, which increases with age. Branch color is Dark Reddish Orange 178B. The number of lenticels per given area (number/cm$^2$) is 0.6. Lenticel length (mm) and diameter (mm) are 4.7 and 1.4, respectively.

One-year old shoots of 'Himari' have a length (cm) of 52.3 and diameter (mm) of 13.4. The texture of new growth is relatively smooth. Mature growth is medium rough. Roughness increases with age. The color is Brownish grey N200B. Internode length is 3.8 cm. The number of lenticels per give area is 1.0/cm$^2$. Lenticel length (mm) and diameter (mm) are 2.5 and 0.9, respectively. Current-season shoots have a length (cm) of 37.9 and diameter (mm) of 4.8. and are Strong Yellow Green 144A. Internode length is 3.8 cm. The number of lenticels per area for current-season shoots is 2.2; and lenticel length (mm) and diameter (mm) are 1.4 and 0.8, respectively. Young shoots have a slightly weak anthocyanin coloration at apex.

'Himari' leaves are elliptic in shape, with a length of 16.4 cm and with of 6.9 cm. The apex is acute. The leaf margin is serrate and the base is round. The upper surface is relatively smooth. Leaves have a pinnate venation pattern. The front side of the leaf is Greyish Olive Green NN137A and the back side of is Moderate Yellowish Green 138A.

'Himari' petioles are Dark Red 187A in color with a length (mm) and diameter (mm) of 30.3 and 2.2, respectively.

Stipules have a Greyish Red 178A color and the number of stipules is usually 2. Stipule length is 6.8 mm.

There are usually two glands. Glands are reniform in shape. The length and width are 3.2 mm and 2.9 mm, respectively. Gland color is Dark Reddish Orange 178B.

The fruit of 'Himari' is 24.0 mm in height. The first picking date is about July 17 and the last about July 31. The stalk is 31.6 mm in length with a diameter of 1.8 mm with a Strong Yellow Green 143B color. 'Himari' fruit has thick skin with a tendency to crack when exposed to rain during harvest time. The skin of the fruit is Strong Red 46A in color and has a smooth texture. Lenticels are abundant in number. Fruit firmness is medium to firm. The texture is firm. The fruit flesh is semi-free with respect to adherence to skin. The fruit flesh color is Light Yellow 14D. Juice flavor is sweet with a pleasing acid/sugar balance. Juice is Brilliant Yellow 20A in color. The fruit stone is broad elliptic in shape and is semi-free. The stone length is 12.1 mm, depth is 9.9 mm, and thickness is 7.6 mm. The stone apex is rounded with a flat base. The stone does not have a tendency to split and the color is Moderate Orange N167C.

Test Results in Growing Fields

Test results in growing fields were obtained as follows. Grafting was in 2013 and the planting year was 2014. In the case of grafting, the following year is considered the first year. The rootstock employed was 'Colt' (U.S. Plant Pat. No. 4,059). Plants were planted at a distance of 5×4 meters. The number of repeat trees was three. Rain cover was present. The tree form was the main trunk form and other cultivation management was in accordance with conventional practices. For grafting, there were five trees for 'HC10'. The number of trees tested for each year from 2014-2021 is shown in Table 2. There were cases where snow damage, animal damage, and tree vigor decay caused tree death, resulting in a decrease in number of test trees from the time of planting.

TABLE 2

| Number of tested trees | | | | | | | | |
|---|---|---|---|---|---|---|---|---|
| | Test Year | | | | | | | |
| Variety | 2014 | 2015 | 2016 | 2017 | 2018 | 2019 | 2020 | 2021 |
| 'HC10' | 5 | 5 | 5 | 5 | 5 | 3 | 3 | 3 |
| 'Sato Nishiki' | 3 | 3 | 3 | 3 | 3 | 3 | 3 | 3 |
| 'Nanyo' | 3 | 3 | 3 | 3 | 3 | 3 | 3 | 2 |
| 'Benishuho' | 3 | 3 | 3 | 3 | 3 | 3 | 2 | 2 |

Trunk circumference was measured at a height of 10 cm above the grafting portion. The tree height is the maximum tree height. Tree width is the maximum width of the crown, averaged in row and inter-row directions. The length, thickness and direction of elongation of young shoots were compared. Young shoot length was measured at the tip of offshoot at a height slightly above eye levels (about 5 to 8 shoots).

Growth stages were assessed as follows. Germination stage was observed when three or more leaf buds having loosened scales and initial green were found on offshoots. The blooming stage was considered to begin when continuous blooming began. Full bloom was considered to be when about 80% of blossoms bloomed. More than 80% of bloom shedding was considered to be when petals fall. The harvest stage "prime" was considered to be the day when yield exceeded half.

Productivity was determined as follows. Bouquet spurs observations were based on the density and number of bouquet spurs attached to branches of 2 years or older. The number of floral buds per bouquet spur were assessed on a scale of 1 to 5 with less than or equal to 3 being assessed as "1", about 5 being assessed as "3" and 7 or more being assessed as "5". The number of fruits per bouquet spur was the average number of fruit among about 100 spurs at a height slightly above eye level. The yield is the value obtained by multiplying the number of fruits by average fruit weight (kg).

Characteristics considered in evaluating fruit quality included fruit cracking on tree, varying from "0" (None) to "5" (Extreme); Uniformity of fruit size (from "1" (Poor) to "5" (Good)); average transverse diameter of fruit; fruit size (average weight); skin coloration from "1" (Weak) to "5" (Strong). Skin thickness (Thin to Thick) and fruit firmness (Soft to Firm) was based on sensory analysis. Maximum breaking stress of flesh was measured using a texture analyzer (TA.XT plusC). when a plunger with diameter of 3 mm was pierced at 2 mm/sec on peeled equatorial portion of fruit in transverse diameter direction of fruit core (15 fruits each time). Acidity was assessed in terms of malic acid converted from titration value of 10 or more squeezed mature fruits from "1" (Low) to "5" (High). Sensory evaluations was also performed for acidity, sweetness, and juiciness of mature fruit.

Tree growth and vigor are shown in Table 3 and Tables 4A and B below. The comparison showed that 'HC10' was less than 'Nanyo' and equivalent to 'Sato Nishiki' in trunk circumference. The tree vigor was "medium to strong", which was slightly weaker than 'Nanyo'. The tree habit was "spreading" and the tree branching was "weak to medium". The young shoot length at tip of offshoot was short. The ratio of young shoots/offshoots was small to medium.

TABLE 3

| Tree growth | | | | | | | | |
|---|---|---|---|---|---|---|---|---|
| | | Year (tree age) | | | | | | |
| | Variety | 2015 (3) | '16 (4) | '17 (5) | '18 (6) | 19 (7) | '20 (8) | '21 (9) |
| Trunk circumference (cm) | 'HC10' | 9.1 | 14.8 | 21.7 | 26.8 | 32.5 | 40.4 | 45.2 |
| | 'Sato Nishiki' | 8.0 | 13.4 | 20.8 | 28.2 | 35.0 | 42.5 | 48.6 |
| | 'Nanyo' | 8.5 | 12.2 | 18.0 | 25.4 | 30.4 | 46.6 | 53.4 |
| | 'Benishuho' | 10.2 | 16.5 | 22.6 | 29.0 | 32.4 | 37.8 | 42.7 |
| Tree height (m) | 'HC10' | 2.4 | 3.0 | 3.7 | 3.6 | 4.0 | 4.2 | 4.5 |
| | 'Sato Nishiki' | 2.2 | 3.0 | 3.6 | 4.0 | 4.1 | 4.2 | 4.6 |
| | 'Nanyo' | 1.5 | 2.4 | 2.9 | 3.3 | 3.6 | 4.6 | 5.0 |
| | 'Benishuho' | 2.3 | 2.8 | 3.5 | 3.6 | 3.7 | 4.3 | 4.2 |
| Tree width (m) | 'HC10' | 0.8 | 1.2 | 2.0 | 2.5 | 3.2 | 3.7 | 4.0 |
| | 'Sato Nishiki' | 0.6 | 1.1 | 1.7 | 2.3 | 2.7 | 3.5 | 4.0 |
| | 'Nanyo' | 0.6 | 0.9 | 1.4 | 1.9 | 2.5 | 3.9 | 4.3 |
| | 'Benishuho' | 0.7 | 1.2 | 1.8 | 2.5 | 2.7 | 3.3 | 4.1 |

The value represents an average of all tested trees (the same applies hereinafter).

TABLE 4A

Comparison of tree vigor and tree habit, 2019-2021.
Tree vigor values range from 1 (weak) to 5 (strong).
Tree habit values range from 1 (upright) to 5 (spreading)

| Tree vigor values | | | | | |
|---|---|---|---|---|---|
| | Year | | | '19 to '21 | |
| Variety | 2019 | 2020 | 2021 | Avg. | Decision |
| 'HC10' | 4.7 | 4.0 | 2.7 | 3.8 | medium to strong |
| 'Sato Nishiki' | 4.7 | 4.7 | 3.7 | 4.3 | strong |
| 'Nanyo' | 5.0 | 5.0 | 4.5 | 4.8 | very strong |
| 'Benishuho' | 3.5 | 4.5 | 3.0 | 3.7 | medium to strong |

| Tree habitvalues | | | | | |
|---|---|---|---|---|---|
| | Year | | | '19 to 21 | |
| Variety | 2019 | 2020 | 2021 | Avg. | Decision |
| 'HC10' | 4.0 | 4.0 | 4.3 | 4.1 | spreading |
| 'Sato Nishiki' | 3.0 | 3.0 | 2.7 | 2.9 | semi-upright |
| 'Nanyo' | 3.7 | 3.0 | 3.5 | 3.4 | semi-upright |
| 'Benishuho' | 3.5 | 3.5 | 4.5 | 3.8 | spreading |

TABLE 4B

Comparison of tree branching (2019-2021),
young shoot length (2020-2021),
number of young shoots/offshoots (2020-2021).
Tree branching values from 1 (weak) to 5 (strong).

| | Tree branching values | | | | | Young shoot length at tip of offshoot (cm) | | |
|---|---|---|---|---|---|---|---|---|
| | Year | | | '19 to '21 | | Year | | '20 to '21 |
| Variety | 2019 | 2020 | 2021 | Avg. | Decision | 2020 | 2021 | Avg. |
| 'HC10' | 4.3 | 3.7 | 3.0 | 3.7 | weak to medium | 48.4 | 51.8 | 50.1 |

TABLE 4B-continued

| Comparison of tree branching (2019-2021), young shoot length (2020-2021), number of young shoots/offshoots (2020-2021). Tree branching values from 1 (weak) to 5 (strong). | | | | | | | | |
|---|---|---|---|---|---|---|---|---|
| 'Sato Nishiki' | 5.0 | 5.0 | 4.0 | 4.7 | medium | 53.5 | 55.3 | 54.4 |
| 'Nanyo' | 4.0 | 5.0 | 4.0 | 4.3 | medium | 64.9 | 67.0 | 66.0 |
| 'Benishuho' | 3.5 | 3.0 | 4.0 | 3.5 | weak to medium | — | — | — |

| | Young shoots/offshoots | | |
|---|---|---|---|
| | Year | | '20 to '21 |
| Variety | 2020 | 2021 | Avg. |
| 'HC10' | 3.3 | 3.2 | 3.3 |
| 'Sato Nishiki' | 4.2 | 4.2 | 4.2 |
| 'Nanyo' | 3.6 | 3.8 | 3.7 |
| 'Benishuho' | — | — | — |

Growth stage and S genotype are shown in Tables 5 and 6. The comparison shows that 'HC10' was equivalent to 'Sato Nishiki' and 'Nanyo' in germination stage. The blooming stage and the harvest stage were "very late" and "late", respectively, equivalent to 'Nanyo', but later than 'Sato Nishiki'. The S genotype of 'HC10' is $S_1S_3$, which differs from $S_3S_6$ of 'Sato Nishiki' and 'Nanyo', $S_1S_6$ of 'Hokko', and $S_4S_6$ of 'Benisbuho'. 'HC10' is thus cross-compatible. In addition, since most of the blooming stages overlap, they function as pollinator trees among each other's cultivars.

TABLE 5

Germination stage, blooming stage, and harvest stage

| | | Germination stage | Blooming stage | | | |
|---|---|---|---|---|---|---|
| | | | Beginning | | Full | Falling |
| Variety | Year | (Month/Day) | (Month/Day) | Decision | (Month/Day) | (Month/Day) |
| 'HC10' | 2019 | 4/17 | 5/9 | | 5/14 | 5/23 |
| | 2020 | 4/4 | 5/12 | | 5/17 | 5/28 |
| | 2021 | 4/3 | 5/12 | | 5/17 | 6/1 |
| | Avg. | 4/8 | 5/11 | very late | 5/16 | 5/28 |
| 'Sato Nishiki' | 2019 | 4/17 | 5/8 | | 5/13 | 5/21 |
| | 2020 | 4/2 | 5/11 | | 5/15 | 5/26 |
| | 2021 | 4/2 | 5/9 | | 5/14 | 5/29 |
| | Avg. | 4/7 | 5/9 | late | 5/14 | 5/25 |
| 'Nanyo' | 2019 | 4/18 | 5/11 | | 5/15 | 5/22 |
| | 2020 | 4/2 | 5/12 | | 5/18 | 5/28 |
| | 2021 | 4/3 | 5/11 | | 5/17 | 5/30 |
| | Avg. | 4/8 | 5/11 | very late | 5/17 | 5/27 |
| 'Benishuho' | 2019 | 4/15 | 5/6 | | 5/11 | 5/21 |
| | 2020 | 4/2 | 5/8 | | 5/13 | 5/22 |
| | 2021 | 3/30 | 5/8 | | 5/14 | 5/24 |
| | Avg. | 4/5 | 5/7 | medium | 5/13 | 5/22 |

TABLE 5-continued

Germination stage, blooming stage, and harvest stage

| | | Harvest stage | | | |
|---|---|---|---|---|---|
| | | Beginning | | Prime | End |
| Variety | Year | (Month/Day) | Decision | (Month/Day) | (Month/Day) |
| 'HC10' | 2019 | 7/15 | | 7/20 | 7/26 |
| | 2020 | 7/16 | | 7/23 | 7/31 |
| | 2021 | 7/19 | | 7/26 | 8/5 |
| | Avg. | 7/17 | late | 7/23 | 7/31 |
| 'Sato Nishiki' | 2019 | 7/1 | | 7/4 | 7/8 |
| | 2020 | 7/1 | | 7/5 | 7/10 |
| | 2021 | 7/7 | | 7/10 | 7/15 |
| | Avg. | 7/3 | medium | 7/6 | 7/11 |
| 'Nanyo' | 2019 | 7/15 | | 7/20 | 7/25 |
| | 2020 | 7/16 | | 7/20 | 7/24 |
| | 2021 | 7/22 | | 7/26 | 7/30 |
| | Avg. | 7/18 | late | 7/22 | 7/26 |
| 'Benishuho' | 2019 | 7/8 | | 7/15 | 7/22 |
| | 2020 | 7/13 | | 7/20 | 7/27 |
| | 2021 | 7/12 | | 7/19 | 7/26 |
| | Avg. | 7/11 | medium to late | 7/18 | 7/25 |

Note:
The emphasized portion indicates the standard state of the variety according to the Examination Guidelines for Agricultural, Forest, or Aquatic Plant Species.

TABLE 6

S Genotyping Results (Central Station, Biotechnology Group, 2016)

| | S genotype | | | | | | | | | |
|---|---|---|---|---|---|---|---|---|---|---|
| Variety | $S_1$ | $S_2$ | $S_3$ | $S_4$ | $S_{4'}$ | $S_5$ | $S_6$ | $S_7$ | $S_9$ | $S_{10}$ |
| 'HC10' | + | | + | | | | | | | |
| 'Sato Nishiki' | | | + | | | | + | | | |
| 'Nanyo' | | | + | | | | + | | | |
| 'Hokko' | + | | | | | | + | | | |
| 'Benishuho' | | | | + | | | + | | | |

| | S genotype | | | | Genotype decision | Cultivated area ratio (%)[1)] |
|---|---|---|---|---|---|---|
| Variety | $S_{12}$ | $S_{13}$ | $S_{14}$ | $S_{16}$ | | (2018) |
| 'HC10' | | | | | $S_1S_3$ | — |
| 'Sato Nishiki' | | | | | $S_3S_6$ | 46 |
| 'Nanyo' | | | | | $S_3S_6$ | 16 |
| 'Hokko' | | | | | $S_1S_6$ | 25 |
| 'Benishuho' | | | | | $S_4S_6$ | 7 |

[1)]Ratio of Cultivation Area in Hokkaido according to the 2018 Production Trends of Specialty Fruit Trees Research (Ministry of Agriculture, Forestry and Fisheries).

Blooming and yield results are shown in Tables 7 and 8. The density of bouquet spurs of 'HC10' was "medium", which is more than 'Nanyo' and lower than 'Sato Nishiki'. 'HC10' was equivalent to 'Nanyo' in floral buds per bouquet spur. The number of fruits per bouquet spur was larger than that of 'Nanyo' and less than that of 'Sato Nishiki'. The fruiting age was 5 or 6 years, equivalent to 'Sato Nishiki' and 'Nanyo'. 'HC10' was larger than 'Nanyo' and less than 'Sato Nishiki' in the number of fruits per tree. 'HC10' was larger than 'Nanyo' and less than 'Sato Nishiki' in yield.

TABLE 7

Bouquet spurs values (1 weak to 5 strong), floral buds, and fruit-setting property

| Variety | Bouquet spurs (1 weak to 5 strong) 2019 | Year 2020 | 2021 | '19 to '21 Avg. | Decision |
|---|---|---|---|---|---|
| 'HC10' | 3.0 | 2.7 | 2.3 | 2.7 | medium |
| 'Sato Nishiki' | 4.7 | 5.0 | 4.0 | 4.6 | strong |
| 'Nanyo' | 1.0 | 2.3 | 2.0 | 1.8 | weak |
| 'Benishuho' | 3.5 | 4.0 | 4.0 | 3.8 | medium to strong |

| Variety | Floral buds per bouquet spur[1)] (1 weak to 5 strong) | Number of fruits per bouquet spur[1)] (pieces) |
|---|---|---|
| 'HC10' | 1.0 | 1.4 |
| 'Sato Nishiki' | 2.7 | 2.4 |
| 'Nanyo' | 1.0 | 0.6 |
| 'Benishuho' | 2.5 | 3.0 |

[1)]Researched only in 2021

TABLE 8

Number of fruits produced and yield per tree

| Variety | Number of fruits (/tree) Test Year (tree age) 2015 (3) | '16 (4) | '17 (5) | '18 (6) | '19 (7) | '20 (8) | '21 (9) |
|---|---|---|---|---|---|---|---|
| 'HC10' | 1 | 0 | 1 | 1 | 224 | 427 | 303 |
| 'Sato Nishiki' | 0 | 0 | 0 | 29 | 577 | 563 | 1331 |
| 'Nanyo' | 0 | 0 | 0 | 3 | 83 | 91 | 342 |
| 'Benishuho' | 0 | 0 | 1 | 43 | 1299 | 814 | 1288 |

| Variety | Yield (kg/tree)[1)] Test Year (tree age) '19 (7) | '20 (8) | '21 (9) | Cumulative yield | Cumulative yield relative to control (%) | Cumulative yield relative to standard (%) |
|---|---|---|---|---|---|---|
| 'HC10' | 2.1 | 4.7 | 3.5 | 10.4 | 198 | 54 |
| 'Sato Nishiki' | 4.0 | 4.3 | 11.0 | 19.2 | 366 | (100) |
| 'Nanyo' | 0.9 | 0.9 | 3.5 | 5.3 | (100) | 27 |
| 'Benishuho' | 9.0 | 7.0 | 11.2 | 27.2 | 518 | 142 |

[1)]Yield was calculated by fruit number × fruit size.

In fruit quality observations determined at prime of harvest (see, Tables 9A and 9B), the fruit transverse diameter of 'HC10' was 28.6 mm, which was larger than those of 'Sato Nishiki', 'Nanyo', and 'Benishuho'. The fruit weight was 10.7 g and "very large", equivalent to 'Nanyo', indicating a large size line. The skin coloration was "medium to strong", which was obviously stronger than 'Nanyo' and was equivalent to 'Sato Nishiki'. The skin thickness was "thick", which was thicker than 'Sato Nishiki' and 'Nanyo'. The fruit firmness was "medium to firm", which was firmer than 'Sato Nishiki' and 'Nanyo' and softer than 'Benishuho'. The acidity was higher than those of 'Nanyo' and 'Benishuho' and equivalent to 'Sato Nishiki'. The sugar content was 21.5° Brix, which was higher than those of 'Sato Nishiki' and 'Nanyo' and slightly lower than that of 'Benishuho'. In the sensory analysis, the fruit acidity was "low", equivalent to 'Sato Nishiki' and 'Nanyo'. The sweetness was "medium to high", which was higher than those of 'Sato Nishiki' and 'Nanyo' and slightly lower than 'Benishuho'. The fruit juiciness was "strong", equivalent to 'Sato Nishiki' and 'Nanyo'. The stone size was "small", which was smaller than those of 'Sato Nishiki' and 'Nanyo'. The ratio of fruit size to the stone was "large".

TABLE 9A

Fruit quality at prime of harvest. Skin coloration values range from 1 (weak) to 5 (strong). Skin thickness values range from 1 (thing) to 5 (thick). Fruit firmness values range from 1 (soft) to 5 (firm).

| Variety | Year | Fruit transverse diameter (mm) | Fruit size (g) | Decision | Skin coloration (1-5) | Decision |
|---|---|---|---|---|---|---|
| 'HC10' | 2019 | 29.0 | 9.7 | | 3.8 | |
| | 2020 | 27.9 | 11.0 | | 3.8 | |
| | 2021 | 29.0 | 11.5 | | 3.3 | |
| | Avg. | 28.6 | 10.7 | very large | 3.6 | medium to strong |
| 'Sato Nishiki' | 2019 | 25.6 | 7.0 | | 4.0 | |
| | 2020 | 24.0 | 7.6 | | 4.0 | |
| | 2021 | 24.9 | 8.2 | | 3.7 | |
| | Avg. | 24.8 | 7.6 | medium | 3.9 | medium to strong |
| 'Nanyo' | 2019 | 27.6 | 10.0 | | 2.5 | |
| | 2020 | 25.4 | 9.1 | | 2.0 | |
| | 2021 | 26.0 | 9.6 | | 2.5 | |
| | Avg. | 26.3 | 9.6 | very large | 2.3 | weak to medium |
| 'Benishuho' | 2019 | 24.8 | 6.7 | | 3.3 | |
| | 2020 | 25.5 | 8.4 | | 4.0 | |
| | 2021 | 26.4 | 8.8 | | 2.5 | |
| | Avg. | 25.6 | 7.9 | medium | 3.3 | medium |

| Variety | Year | Skin thickness (1-5) | Decision | Fruit firmness (1-5) | Decision | Maximum breaking stress of flesh[1)] (g) (g) |
|---|---|---|---|---|---|---|
| 'HC10' | 2019 | 5.0 | | 3.2 | | — |
| | 2020 | 5.0 | | 3.7 | | — |
| | 2021 | 5.0 | | 2.7 | | 74.3 |
| | Avg. | 5.0 | thick | 3.2 | medium to firm | — |
| 'Sato Nishiki' | 2019 | 2.7 | | 1.7 | | — |
| | 2020 | 4.7 | | 2.3 | | — |
| | 2021 | 3.0 | | 2.0 | | 70.2 |
| | Avg. | 3.4 | medium | 2.0 | medium | — |
| 'Nanyo' | 2019 | 3.5 | | 2,0 | | — |
| | 2020 | 5.0 | | 1.0 | | — |
| | 2021 | 4.0 | | 2.0 | | 52.9 |
| | Avg. | 4.2 | medium to thick | 1.7 | soft to medium | — |
| 'Benishuho' | 2019 | 4.8 | | 4.0 | | — |
| | 2020 | 5.0 | | 5.0 | | — |
| | 2021 | 4.5 | | 3.5 | | 95.1 |
| | Avg. | 4.8 | thick | 4.2 | firm | — |

TABLE 9B

Fruit quality at prime of harvest. Acidity, Sweetness, Juiciness, Stone size, Ratio of weight of fruit to weight of stone. Fruit acidity values range from 1 (low) to 5 (high). Fruit sweetness values range from 1 (low) to 5 (high). Fruit juiciness values range from 1 (weak) to 5 (strong).

| Variety | Year | Acidity (g/100 mL) | Sugar content (° Brix) | Sugar acid ratio | Fruit acidity (1-5) | Fruit acidity Decision | Fruit sweetness (1-5) | Fruit sweetness Decision |
|---|---|---|---|---|---|---|---|---|
| 'HC10' | 2019 | 0.61 | 20.1 | 33.0 | 1.8 | | 3.3 | |
| | 2020 | 0.58 | 21.9 | 37.8 | 2.3 | | 3.8 | |
| | 2021 | 0.60 | 22.5 | 37.5 | 2.0 | | 3.7 | |
| | Avg. | 0.60 | 21.5 | 36.0 | 2.1 | low | 3.6 | medium to high |
| 'Sato Nishiki' | 2019 | 0.54 | 19.1 | 35.4 | 2.0 | | 3.3 | |
| | 2020 | 0.56 | 17.6 | 31.4 | 1.7 | | 3.0 | |
| | 2021 | 0.58 | 18.6 | 32.1 | 2.0 | | 3.3 | |
| | Avg. | 0.56 | 18.4 | 32.9 | 1.9 | low | 3.2 | medium |
| 'Nanyo' | 2019 | 0.53 | 18.0 | 34.0 | 1.0 | | 3.0 | |
| | 2020 | 0.46 | 21.6 | 47.0 | 1.0 | | 4.0 | |
| | 2021 | 0.53 | 20.0 | 37.7 | 3.0 | | 2.0 | |
| | Avg. | 0.51 | 19.9 | 39.2 | 1.7 | low | 3.0 | medium |
| 'Benishuho' | 2019 | 0.49 | 20.8 | 42.4 | 1.4 | | 3.6 | |
| | 2020 | 0.49 | 24.5 | 50.0 | 1.3 | | 5.0 | |
| | 2021 | 0.40 | 21.2 | 53.0 | 1.0 | | 3.0 | |
| | Avg. | 0.46 | 22.2 | 48.2 | 1.2 | low | 3.9 | high |

| Variety | Year | Fruit juiciness (1-5) | Fruit juiciness Decision | Stone size[3)] (g) | Stone size Decision | Ratio weight of fruit/weight of stone | Ratio weight Decision |
|---|---|---|---|---|---|---|---|
| 'HC10' | 2019 | 3.8 | | — | | — | |
| | 2020 | 4.0 | | 0.33 | | 33.3 | |
| | 2021 | 5.0 | | 0.31 | | 37.5 | |
| | Avg. | 4.3 | strong | 0.32 | small | 35.4 | large |
| 'Sato Nishiki' | 2019 | 3.3 | | — | | — | |
| | 2020 | 4.7 | | 0.41 | | 18.5 | |
| | 2021 | 4.7 | | 0.37 | | 22.4 | |
| | Avg. | 4.2 | strong | 0.39 | medium | 20.5 | small |
| 'Nanyo' | 2019 | 3.8 | | — | | — | |
| | 2020 | 5.0 | | 0.38 | | 23.9 | |
| | 2021 | 4.5 | | 0.33 | | 29.4 | |
| | Avg. | 4.4 | strong | 0.35 | small to medium | 26.7 | medium |
| 'Benishuho' | 2019 | 2.8 | | — | | — | |
| | 2020 | 3.0 | | 0.34 | | 24.7 | |
| | 2021 | 3.3 | | 0.39 | | 22.6 | |
| | Avg. | 3.0 | medium | 0.37 | medium | 23.6 | small to medium |

[1)]measured only in 2021.

Incidence of cold damage, frost damage, and disease and pestilence were also evaluated. Research criteria for cold damage and frost damage are as follows in Table 10. Results are shown in Table 11. Incidence of damage due to *Monilinia kusanoi, Monilinia fructicola, Rhacochlaena japonica*, and *Drosophila suzukii* was also assessed. The incidence of cold damage of 'HC10' was more than that of 'Hokko' and equivalent to those of 'Sato Nishiki', 'Nanyo', and 'Benishuho'. The incidence of frost damage was equivalent to those of 'Sato Nishiki', 'Nanyo', and 'Benishuho'. There was no incidence of disease and pest infestation. No damage due to *Monilinia kusanoi, Monilinia fructicola, Rhacochlaena japonica*, or *Drosophila suzukii* was observed, or was damage due to other diseases or pests observed.

TABLE 10

Criteria employed for assessment cold damage (values from 1-5) and frost damage (percentage of pistil loss)

| Items | Research Criteria | Research | Unit |
|---|---|---|---|
| Degree of cold damage | The degree of cold damage during the winter period is evaluated by observation.<br>0: none<br>1: death of part of floral buds (without influence on yield)<br>2: death of many floral buds (with influence on yield)<br>3: death of leaf buds (spur leaf buds)<br>4: death of branches (vegetative branch leaf buds)<br>5: death | observation | |
| Degree of frost damage | The degree of frost damage in early spring is evaluated based on the degree of pistil loss.<br>0: 0%; 1: ~20%; 2: 20 to 40%; 3: 40 to 60%; 4: 60 to 80%; 5: 80%~ | observation | |

TABLE 11

Incidence of cold damage and frost damage

| Variety | Incidence of cold damage (0 None to 5 Extreme) Year 2019 | 2020 | 2021 | Incidence of frost damage (0 None to 5 Extreme) Year 2019 | 2020 | 2021 |
|---|---|---|---|---|---|---|
| 'HC10' | 0.0 | 0.0 | 1.3 | 0.0 | 0.0 | 1.0 |
| 'Sato Nishiki' | 0.0 | 0.0 | 1.0 | 0.0 | 0.0 | 1.0 |
| 'Nanyo' | 0.0 | 0.0 | 1.5 | 0.0 | 0.0 | 1.0 |
| 'Benishuho' | 0.0 | 0.0 | 1.5 | 0.0 | 0.0 | 1.0 |
| 'Hokko'[1)] | 0.0 | 0.0 | 0.0 | 0.0 | 0.0 | 1.0 |

[1)]used only in this research as a standard variety having a cold hardiness of "strong"

Additional Trial Results

Additional test results are presented below of test locations Fukagawa City, Japan, Mashike Town, Japan, and Yoichi Town, Japan. The planting scheme and number of tested trees are shown in Table 12.

TABLE 12

Planting

| Test location | Grafting year | Settled planting year | Rootstock | Planting Distance | Number of repeat trees | Rain cover |
|---|---|---|---|---|---|---|
| Fukagawa City | 2013 | 2014 | 'Colt' | 6 × 4 m | 3 | present |

TABLE 12-continued

| Planting | | | | | |
|---|---|---|---|---|---|
| Mashike Town | 2014 | 2015 | 'Colt' 7 × 3.6 m | 3 | present |
| Yoichi Town | 2013 | 2014 | 'Colt' 7.2 × 3.6 m | 3 | present |

| Test location | Variety | Test Year 2014 | 2015 | 2016 | 2017 |
|---|---|---|---|---|---|
| Fukagawa City | 'HC10' | 3 | 3 | 3 | 3 |
| | 'Sato Nishiki' | 3 | 2 | 2 | 2 |
| | 'Nanyo' | 3 | 2 | 2 | 2 |
| | 'Benishuho' | 3 | 3 | 3 | 3 |
| Mashike Town | 'HC10' | | 3 | 3 | 3 |
| | 'Sato Nishiki' | | 3 | 3 | 3 |
| Yoichi Town' | 'HC10' | 3 | 3 | 3 | 3 |
| | 'Benishuho' | 3 | 3 | 3 | 3 |
| | 'Sato Nishiki'[1)] | 3 | 2 | 2 | 2 |

| Test location | Variety | Test Year 2018 | 2019 | 2020 | 2021 |
|---|---|---|---|---|---|
| Fukagawa City | 'HC10' | 3 | 3 | 3 | 3 |
| | 'Sato Nishiki' | 2 | 2 | 2 | 2 |
| | 'Nanyo' | 2 | 2 | 2 | 2 |
| | 'Benishuho' | 3 | 3 | 3 | 3 |
| Mashike Town | 'HC10' | 3 | 3 | 3 | 3 |
| | 'Sato Nishiki' | 3 | 3 | 3. | 3 |
| Yoichi Town' | 'HC10' | 3 | 3 | 3 | 3 |
| | 'Benishuho' | 3 | 3 | 3 | 3 |
| | 'Sato Nishiki'[1)] | 1 | 1 | 1 | 1 |

There were cases where snow damage, animal damage, and tree vigor decay caused tree death, resulting in a decrease in number of test trees from the time of planting.
[1)]excluded from the results and treated as reference data because of reduction of test trees due to snow damage and animal damage in addition to development of Agrobacterium tumefaciens in remaining trees.

The same criteria were employed for these evaluations as described above. The results (Tables 13 and 14) showed that 'HC10' was larger than 'Sato Nishiki' and 'Nanyo' and equivalent to or slightly larger than 'Benishuho' in trunk circumference. The tree vigor was slightly stronger than that of 'Sato Nishiki' and equivalent to that of 'Nanyo'.

TABLE 13

| Tree growth | | | | | | |
|---|---|---|---|---|---|---|
| | | | Year (tree age)[1)] | | | |
| Items | Test location | Variety | 2015 (3) | '16 (4) | '17 (5) | '18 (6) |
| Trunk circum - ference (cm) | Fukagawa City | 'HC10' | 9.3 | 15.2 | 22.2 | 33.0 |
| | | 'Sato Nishiki' | 7.0 | 12.6 | 18.0 | 24.6 |
| | | 'Nanyo' | 9.2 | 13.3 | 18.0 | 25.1 |
| | | 'Benishuho' | 10.8 | 17.9 | 24.0 | 32.8 |
| | Mashike Town | 'HC10' | 5.8 | 8.0 | 13.8 | 20.1 |
| | | 'Sato Nishiki' | 4.1 | 5.4 | 9.0 | 12.8 |
| | Yoichi Town' | 'HC10' | 9.2 | 16.0 | 22.8 | 32.3 |
| | | 'Benishuho' | 10.5 | 17.4 | 23.6 | 30.0 |
| | | 'Sato Nishiki' | 7.9 | 13.3 | 15.4 | 23.3 |

TABLE 13-continued

| Tree growth | | | | | | |
|---|---|---|---|---|---|---|
| Tree height (m) | Fukagawa City | 'HC10' | 2.1 | 3.0 | 3.6 | 4.0 |
| | | 'Sato Nishiki' | 1.2 | 2.5 | 3.0 | 3.4 |
| | | 'Nanyo' | 1.7 | 3.1 | 3.6 | 4.2 |
| | | 'Benishuho' | 2.5 | 3.4 | 3.7 | 4.1 |
| | Mashike Town | 'HC10' | 1.8 | 2.2 | 3.0 | 4.0 |
| | | 'Sato Nishiki' | 1.2 | 1.5 | 2.4 | 3.0 |
| | Yoichi Town | 'HC10' | 2.1 | 3.4 | 4.3 | 5.1 |
| | | 'Benishuho' | 2.1 | 3.0 | 4.1 | 4.7 |
| | | 'Sato Nishiki' | 1.2 | 2.3 | 3.7 | 4.5 |
| Tree width (m) | Fukagawa City' | 'HC10' | 1.2 | 1.6 | 2.6 | 3.5 |
| | | 'Sato Nishiki' | 0.6 | 1.0 | 1.6 | 2.3 |
| | | 'Nanyo' | 1.2 | 1.1 | 2.2 | 2.6 |
| | | 'Benishuho' | 0.6 | 1.7 | 2.6 | 3.4 |
| | Mashike Town | 'HC10' | 0.2 | 0.7 | 1.4 | 2.1 |
| | | 'Sato Nishiki' | 0.2 | 0.4 | 0.9 | 1.1 |
| | Yoichi Town | 'HC10' | 0.8 | 1.7 | 2.7 | 3.1 |
| | | 'Benishuho' | 0.8 | 1.5 | 2.3 | 2.8 |
| | | 'Sato Nishiki' | 0.3 | 0.9 | 1.4 | 2.1 |

| Items | Test location | Variety | Year (tree age)[1)] '19 (7) | '20 (8) | '21 (9) |
|---|---|---|---|---|---|
| Trunk circum - ference (cm) | Fukagawa City | 'HC10' | 38.0 | 42.9 | 47.8 |
| | | 'Sato Nishiki' | 29.3 | 32.0 | 34.7 |
| | | 'Nanyo' | 29.0 | 32.5 | 36.2 |
| | | 'Benishuho' | 36.9 | 40.5 | 45.1 |
| | Mashike Town | 'HC10' | 26.3 | 31.7 | 37.2 |
| | | 'Sato Nishiki' | 16.4 | 20.0 | 26.0 |
| | Yoichi Town' | 'HC10' | 35.9 | 42.0 | 49.2 |
| | | 'Benishuho' | 33.1 | 38.6 | 43.3 |
| | | 'Sato Nishiki' | 27.0 | 31.0 | 37.3 |
| Tree height (m) | Fukagawa City | 'HC10' | 3.8 | 4.2 | 4.2 |
| | | 'Sato Nishiki' | 3.4 | 3.7 | 3.8 |
| | | 'Nanyo' | 3.8 | 3.8 | 4.4 |
| | | 'Benishuho' | 3.7 | 4.0 | 4.5 |
| | Mashike Town | 'HC10' | 4.2 | 4.4 | 4.5 |
| | | 'Sato Nishiki' | 3.3 | 3.7 | 3.7 |
| | | 'HC10' | 4.4 | 4.2 | 4.2 |
| | Yoichi Town | 'Benishuho' | 3.9 | 4.2 | 3.7 |
| | | 'Sato Nishiki' | 4.2 | 4.0 | 3.4 |
| Tree width (m) | Fukagawa City' | 'HC10' | 3.9 | 4.6 | 5.1 |
| | | 'Sato Nishiki' | 2.5 | 2.6 | 3.2 |
| | | 'Nanyo' | 2.8 | 3.5 | 4.2 |
| | | 'Benishuho' | 3.8 | 4.1 | 5.0 |
| | Mashike Town | 'HC10' | 2.6 | 3.3 | 4.2 |
| | | 'Sato Nishiki' | 1.3 | 1.8 | 2.2 |
| | Yoichi Town | 'HC10' | 3.8 | 4.6 | 5.1 |
| | | 'Benishuho' | 3.8 | 4.5 | 5.0 |
| | | 'Sato Nishiki' | 2.1 | 2.6 | 3.1 |

[1)]2- to 8-year trees only in Mashike Town

TABLE 14

| Tree vigor | | | | | |
|---|---|---|---|---|---|
| | | Tree vigor (1 weak to 5 strong) | | | |
| | | Year | | | '19 to '21 |
| Test location | Variety | 2019 | 2020 | 2021 | Avg. |
| Fukagawa City | 'HC10' | 5.0 | 4.7 | 4.7 | 4.8 |
| | 'Sato Nishiki' | 4.5 | 4.5 | 3.7 | 4.2 |
| | 'Nanyo' | 5.0 | 5.0 | 5.0 | 5.0 |
| | 'Benishuho' | 4.7 | 4.3 | 3.7 | 4.2 |
| Mashike Town | 'HC10' | 4.3 | 3.0 | 3.3 | 3.6 |
| | 'Sato Nishiki' | 2.3 | 2.3 | 1.3 | 2.0 |
| Yoichi Town | 'HC10' | 4.0 | 3.3 | 3.3 | 3.6 |
| | 'Benishuho' | 3.0 | 2.3 | 3.0 | 2.8 |
| | 'Sato Nishiki' | 4.0 | 2.0 | 2.0 | 2.7 |

Growth stage comparison results are shown in Tables 15-17. The results showed that 'HC10' was slightly later than 'Benishuho' in germination stage and equivalent to 'Sato Nishiki' and 'Nanyo'. The blooming stage was equivalent to those of 'Sato Nishiki' and 'Nanyo'. Since most of the blooming stages overlap, there is no problem for pollen exchange. The beginning of fruit ripening was 15 to 17-day later than "medium" of 'Sato Nishiki' and equivalent to or slightly later than 'Nanyo'.

TABLE 15

Germination stage, Blooming stage, and Harvest stage (Fukagawa City)

| Variety | Year | Germination stage (Month/Day) | Blooming stage: Beginning (Month/Day) | Blooming stage: Full (Month/Day) | Blooming stage: Falling (Month/Day) |
|---|---|---|---|---|---|
| 'HC10' | 2019 | 4/14 | 5/8 | 5/16 | 5/23 |
| | 2020 | 4/9 | 5/10 | 5/13 | 5/27 |
| | 2021 | 4/12 | 5/12 | 5/16 | 5/26 |
| | Avg. | 4/12 | 5/10 | 5/15 | 5/25 |
| 'Sato Nishiki' | 2019 | 4/14 | 5/7 | 5/14 | 5/22 |
| | 2020 | 4/7 | 5/10 | 5/13 | 5/25 |
| | 2021 | 4/16 | 5/11 | 5/15 | 5/23 |
| | Avg. | 4/12 | 5/9 | 5/14 | 5/23 |
| 'Nanyo' | 2019 | 4/14 | 5/8 | 5/16 | 5/23 |
| | 2020 | 4/9 | 5/11 | 5/13 | 5/27 |
| | 2021 | 4/14 | 5/12 | 5/17 | 5/26 |
| | Avg. | 4/12 | 5/10 | 5/15 | 5/25 |
| 'Benishuho' | 2019 | 4/14 | 5/5 | 5/12 | 5/22 |
| | 2020 | 4/7 | 5/9 | 5/11 | 5/23 |
| | 2021 | 4/12 | 5/8 | 5/11 | 5/21 |
| | Avg. | 4/11 | 5/7 | 5/11 | 5/22 |

| Variety | Year | Harvest stage: Beginning (Month/Day) | Harvest stage: Prime (Month/Day) | Harvest stage: End (Month/Day) |
|---|---|---|---|---|
| 'HC10' | 2019 | 7/17 | 7/22 | 7/25 |
| | 2020 | 7/31 | 8/2 | 8/4 |
| | 2021 | 7/25 | 7/25 | 8/4 |
| | Avg. | 7/24 | 7/27 | 8/1 |
| 'Sato Nishiki' | 2019 | 6/26 | 7/3 | 7/11 |
| | 2020 | 7/12 | 7/15 | 7/19 |
| | 2021 | 7/14 | 7/17 | 7/20 |
| | Avg. | 7/7 | 7/12 | 7/17 |
| 'Nanyo' | 2019 | 7/14 | 7/20 | 7/27 |
| | 2020 | 7/23 | 7/27 | 8/1 |
| | 2021 | 7/21 | 7/25 | 7/28 |
| | Avg. | 7/19 | 7/24 | 7/29 |
| 'Benishuho' | 2019 | 7/7 | 7/13 | 7/20 |
| | 2020 | 7/15 | 7/23 | 8/1 |
| | 2021 | 7/16 | 7/21 | 7/27 |
| | Avg. | 7/13 | 7/19 | 7/26 |

TABLE 16

Germination stage, Blooming stage, and Harvest stage (Mashike Town)

| Variety | Year | Germination stage (Month/Day) | Blooming stage: Beginning (Month/Day) | Blooming stage: Full (Month/Day) | Blooming stage: Falling (Month/Day) |
|---|---|---|---|---|---|
| 'HC10' | 2019 | 4/11 | 5/6 | 5/10 | 5/22 |
| | 2020 | 4/1 | — | — | — |
| | 2021 | 4/11 | 5/7 | 5/11 | 5/20 |
| | Avg. | 4/8 | 5/7 | 5/11 | 5/21 |

TABLE 16-continued

Germination stage, Blooming stage, and Harvest stage (Mashike Town)

| Variety | Year | Germination stage (Month/Day) | Blooming stage: Beginning (Month/Day) | Blooming stage: Full (Month/Day) | Blooming stage: Falling (Month/Day) |
|---|---|---|---|---|---|
| 'Sato Nishiki' | 2019 | 4/10 | 5/6 | 5/11 | 5/24 |
| | 2020 | 4/1 | — | — | — |
| | 2021 | 4/11 | 5/7 | 5/12 | 5/21 |
| | Avg. | 4/7 | 5/7 | 5/12 | 5/23 |

| Variety | Year | Harvest stage: Beginning (Month/Day) | Harvest stage: Prime (Month/Day) | Harvest stage: End (Month/Day) |
|---|---|---|---|---|
| 'HC10' | 2019 | 7/11 | 7/21 | 8/1 |
| | 2020 | 7/13 | 7/19 | 7/26 |
| | 2021 | 7/18 | 7/21 | — |
| | Avg. | 7/14 | 7/20 | 7/29 |
| 'Sato Nishiki' | 2019 | 6/23 | 6/26 | 6/29 |
| | 2020 | 6/28 | 7/2 | 7/5 |
| | 2021 | 7/6 | 7/9 | 7/11 |
| | Avg. | 6/29 | 7/2 | 7/5 |

TABLE 17

Germination stage, Blooming stage, and Harvest stage (Yoichi Town)

| Variety | Year | Germination stage (Month/Day) | Blooming stage: Beginning (Month/Day) | Blooming stage: Full (Month/Day) | Blooming stage: Falling (Month/Day) |
|---|---|---|---|---|---|
| 'HC10' | 2019 | 4/10 | 5/5 | 5/9 | 5/18 |
| | 2020 | 4/15 | 5/6 | 5/13 | 5/25 |
| | 2021 | 4/16 | 5/7 | 5/12 | 5/21 |
| | Avg. | 4/14 | 5/6 | 5/11 | 5/21 |
| 'Benishuho' | 2019 | 4/7 | 5/2 | 5/5 | 5/13 |
| | 2020 | 4/3 | 5/3 | 5/8 | 5/13 |
| | 2021 | 4/7 | 5/1 | 5/7 | 5/16 |
| | Avg. | 4/6 | 5/2 | 5/7 | 5/14 |
| 'Sato Nishiki' | 2019 | 4/13 | 5/5 | 5/9 | 5/17 |
| | 2020 | 4/11 | 5/8 | 5/12 | 5/22 |
| | 2021 | 4/14 | 5/6 | 5/11 | 5/21 |
| | Avg. | 4/13 | 5/6 | 5/11 | 5/20 |

| Variety | Year | Harvest stage: Beginning (Month/Day) | Harvest stage: Prime (Month/Day) | Harvest stage: End (Month/Day) |
|---|---|---|---|---|
| 'HC10' | 2019 | 7/12 | 7/19 | 7/26 |
| | 2020 | 7/17 | 7/22 | 7/27 |
| | 2021 | 7/15 | 7/22 | 7/29 |
| | Avg. | 7/15 | 7/21 | 7/27 |
| 'Benishuho' | 2019 | 7/2 | 7/8 | 7/16 |
| | 2020 | 7/10 | 7/17 | 7/24 |
| | 2021 | 7/9 | 7/15 | 7/22 |
| | Avg. | 7/7 | 7/13 | 7/21 |
| 'Sato Nishiki' | 2019 | 6/22 | 6/29 | 7/6 |
| | 2020 | 7/4 | 7/8 | 7/13 |
| | 2021 | 7/2 | 7/8 | 7/15 |
| | Avg. | 6/29 | 7/5 | 7/11 |

Blooming and yield assessments are shown in Tables 18-21. In the density of bouquet spurs, 'HC10' was higher than 'Sato Nishiki' and 'Benishuho' and slightly higher than 'Nanyo'. In floral buds per bouquet spur, 'HC10' was obviously lower than 'Sato Nishiki' and 'Benishuho' in Fukagawa City and Mashike Town, but equivalent to 'Benishuho' in Yoichi Town. The fruiting age of 'HC10' was 4 or 5 years, equivalent to 'Sato Nishiki' and 'Nanyo'. The yield was equivalent to or larger than 'Sato Nishiki' and obviously larger than 'Nanyo'.

TABLE 18

Bouquet spurs, floral buds, and fruit-setting property

| Test location | Variety | Bouquet spur (1 weak to 5 strong) Year 2019 | 2020 | 2021 | '19 to '21 Avg. |
|---|---|---|---|---|---|
| Fukagawa City | 'HC10' | 4.0 | 2.3 | 2.7 | 3.0 |
| | 'Sato Nishiki' | 5.0 | 4.5 | 4.5 | 4.7 |
| | 'Nanyo' | 4.0 | 1.5 | 2.0 | 2.5 |
| | 'Benishuho' | 5.0 | 5.0 | 4.7 | 4.9 |
| Mashike Town | 'HC10' | 2.0 | 1.3 | 1.7 | 1.7 |
| | 'Sato Nishiki' | 4.7 | 4.7 | 5.0 | 4.8 |
| Yoichi Town | 'HC10' | 4.7 | 3.0 | 4.3 | 4.0 |
| | 'Benishuho' | 5.0 | 5.0 | 4.7 | 4.9 |
| | 'Sato Nishiki' | 5.0 | 4.0 | 4.0 | 4.3 |

| Test location | Variety | Floral buds per bouquet spur[1)] (1 weak to 5 strong) | Number of fruits per bouquet spur[1,2)] (pieces) |
|---|---|---|---|
| Fukagawa City | 'HC10' | 1.0 | 0.3 |
| | 'Sato Nishiki' | 3.0 | 1.2 |
| | 'Nanyo' | 2.0 | 0.1 |
| | 'Benishuho' | 3.3 | 1.5 |
| Mashike Town | 'HC10' | 1.3 | 0.2 |
| | 'Sato Nishiki' | 4.3 | 3.2 |
| Yoichi Town | 'HC10' | 2.0 | 4.3 |
| | 'Benishuho' | 2.3 | 5.3 |
| | 'Sato Nishiki' | 4.0 | 2.8 |

[1)]researched only in 2021.

[2)]partial reduction in the number of fruits due to frost damage in Fukagawa City and Mashike Town

TABLE 19

Number of fruits (A) and yield (B) per tree (Fukagawa City)

(A)

| Variety | Number of fruits (/tree) Test Year (tree age) 2015 (3) | '16 (4) | '17 (5) | '18 (6) | '19 (7) | '20 (8) | '21 (9)[1)] |
|---|---|---|---|---|---|---|---|
| 'HC10' | 0 | 0 | 1 | 11 | 171 | 952 | 225 |
| 'Sato Nishiki' | 0 | 0 | 1 | 54 | 228 | 848 | 286 |
| 'Nanyo' | 0 | 1 | 0 | 14 | 79 | 410 | 48 |
| 'Benishuho' | 3 | 10 | 43 | 160 | 446 | 1854 | 833 |

TABLE 19-continued

Number of fruits (A) and yield (B) per tree (Fukagawa City)

(B)

| Variety | Yield (kg/tree)[2)] Test Year (tree age) '19 (7) | '20 (8) | '21 (9)[1)] | '19 to '21 cumulative yield | Cumulative yield relative to control (%) | Cumulative yield relative to standard (%) |
|---|---|---|---|---|---|---|
| 'HC1'0 | 1.7 | 9.8 | 2.3 | 13.7 | 277 | 177 |
| 'Sato Nishiki' | 1.3 | 4.8 | 1.7 | 7.8 | 157 | (100) |
| 'Nanyo' | 0.6 | 3.9 | 0.4 | 5.0 | (100) | 64 |
| 'Benishuho' | 3.4 | 15.8 | 7.6 | 26.9 | 543 | 346 |

[1)]reduction in the number of fruits and yield due to frost damage

[2)]The yield was calculated by fruit number x fruit size (the same applies to Tables 19 and 20).

TABLE 20

Number of fruits and yield per tree (Mashike Town)

| Variety | Number of fruits (/tree) Test Year (tree age) 2015 (2) | '16 (3) | '17 (4) | '18 (5) | '19 (6) | '20 (7) | '21 (8)[1] |
|---|---|---|---|---|---|---|---|
| 'HC10' | 0 | 0 | 4 | 16 | 159 | 406 | 62 |
| 'Sato Nishiki' | 0 | 0 | 9 | 65 | 187 | 558 | 706 |

| Variety | Yield (kg/tree) Test Year (tree age) '19 (6) | '20 (7) | '21 (8)[1)] | '19 to '21 cumulative yield | Cumulative yield relative to control (%) | Cumulative yield relative to standard (%) |
|---|---|---|---|---|---|---|
| 'HC10' | 1.4 | 3.9 | 0.7 | 6.0 | — | 84 |
| 'Sato Nishiki' | 0.7 | 2.4 | 4.0 | 7.1 | — | (100) |

[1)]reduction in the number of fruits and yield of 'HC10' due to frost damage

TABLE 21

Number of fruits and yield per tree (Yoichi Town)

| Variety | Number of fruits (/tree) Test Year (tree age) 2015 (3) | '16 (4) | '17 (5) | '18 (6) | '19 (7) | '20 (8) | '21 (9) |
|---|---|---|---|---|---|---|---|
| 'HC10' | 0 | 2 | 8 | 90 | 367 | 1429 | 1781 |
| 'Benishuho' | 6 | 29 | 159 | 497 | 1352 | 1333 | 1287 |
| 'Sato Nishiki' | 0 | 9 | 6 | 15 | 298 | 935 | 785 |

TABLE 21-continued

| Number of fruits and yield per tree (Yoichi Town) | | | | | | |
|---|---|---|---|---|---|---|
| | Yield (kg/tree) | | | | Cumulative | Cumulative |
| | Test Year (tree age) | | | '19 to '21 cumu- | yield relative to | yield relative to |
| Variety | '19 (7) | '20 (8) | '21 (9) | lative yield | control (%) | standard (%) |
| 'HC10' | 3.9 | 14.9 | 21.3 | 40.1 | — | — |
| 'Benishuho' | 10.3 | 13.1 | 15.4 | 38.7 | — | — |
| 'Sato Nishiki' | 1.7 | 5.4 | 4.8 | 11.9 | — | — |

Analyses of fruit quality in these trials are shown in Tables 22-24. The fruit transverse diameter of 'HC10' was 26 to 29.1 mm, which was larger than those of 'Sato Nishiki'. 'Nanyo', and 'Benishuho'. The fruit weight was 9.0 to 11.4 g, which was larger than 'Sato Nishiki', 'Nanyo', and 'Benishuho', indicating a large size line. In skin coloration, 'HC10' was equivalent to 'Sato Nishiki' and obviously stronger than 'Nanyo'. The fruit firmness was slightly firmer than those of 'Sato Nishiki' and 'Nanyo'. The acidity was equivalent to or higher than that of 'Sato Nishiki' and higher than 'Nanyo'. The sugar content was 18.5 to 22.9 Brix, which was higher than 'Sato Nishiki' and 'Nanyo' and lower than 'Benishuho'.

TABLE 22

| Fruit quality at prime of harvest (Fukagawa City) | | | | | |
|---|---|---|---|---|---|
| Variety | Test Year | Fruit transverse diameter (mm) | Fruit size (g) | Skin coloration (1 weak to 5 strong) | Fruit firmness (1 soft to 5 firm) |
| 'HC10' | 2019 | 29.1 | 10.1 | 3.0 | 3.0 |
| | 2020 | 27.5 | 10.3 | 2.7 | 2.7 |
| | 2021 | 27.7 | 10.1 | 2.0 | 3.0 |
| | Avg. | 28.1 | 10.1 | 2.6 | 2.9 |
| 'Sato Nishiki' | 2019 | 24.0 | 5.9 | 4.0 | 2.0 |
| | 2020 | 22.0 | 5.7 | 2.0 | 2.0 |
| | 2021 | 21.8 | 5.9 | 2.5 | 3.5 |
| | Avg. | 22.6 | 5.8 | 2.8 | 2.5 |
| 'Nanyo' | 2019 | 25.6 | 7.8 | 2.0 | 3.0 |
| | 2020 | 26.7 | 9.6 | 1.5 | 2.0 |
| | 2021 | 26.0 | 8.8 | 1.0 | 2.3 |
| | Avg. | 26.1 | 8.7 | 1.5 | 2.4 |
| 'Benishuho' | 2019 | 26.5 | 7.7 | 3.8 | 4.3 |
| | 2020 | 26.1 | 8.8 | 3.3 | 4.7 |
| | 2021 | 26.4 | 9.1 | 2.7 | 4.7 |
| | Avg. | 26.3 | 8.5 | 3.3 | 4.6 |

| Variety | Test Year | Maximum breaking stress[1)] (g) | Acidity (g/100 ml) | Sugar content (° Brix) | Sugar acid ratio |
|---|---|---|---|---|---|
| 'HC10' | 2019 | | 0.64 | 21.3 | 33.3 |
| | 2020 | | 0.50 | 18.8 | 37.2 |
| | 2021 | 79.9 | 0.64 | 20.6 | 32.3 |
| | Avg. | | 0.59 | 20.2 | 34.0 |
| 'Sato Nishiki' | 2019 | | 0.63 | 19.7 | 31.3 |
| | 2020 | | 0.52 | 17.3 | 33.5 |
| | 2021 | 95.0 | 0.80 | 19.9 | 25.0 |
| | Avg. | | 0.65 | 19.0 | 29.3 |

TABLE 22-continued

| Fruit quality at prime of harvest (Fukagawa City) | | | | | |
|---|---|---|---|---|---|
| 'Nanyo' | 2019 | | 0.51 | 18.7 | 36.9 |
| | 2020 | | 0.40 | 17.1 | 43.0 |
| | 2021 | 63.7 | 0.53 | 18.9 | 35.7 |
| | Avg. | | 0.48 | 18.2 | 38.1 |
| 'Benishuho' | 2019 | | 0.66 | 26.6 | 40.4 |
| | 2020 | | 0.48 | 21.5 | 44.8 |
| | 2021 | 101.9 | 0.56 | 25.3 | 45.6 |
| | Avg. | | 0.56 | 24.5 | 43.3 |

[1)]researched for maximum breaking stress only in 2021 (the same applies to Tables 22 and 23).

TABLE 23

| Fruit quality at prime of harvest (Mashike Town) | | | | | |
|---|---|---|---|---|---|
| Variety | Test Year | Fruit transverse diameter (mm) | Fruit size (g) | Skin coloration (1 weak to 5 strong) | Fruit firmness (1 soft to 5 firm) |
| 'HC10' | 2019 | 27.8 | 9.0 | 4.0 | 3.3 |
| | 2020 | 26.0 | 9.5 | 4.0 | 4.2 |
| | 2021 | 28.8 | 11.4 | 3.7 | 2.3 |
| | Avg. | 27.5 | 9.9 | 3.9 | 3.3 |
| 'Sato Nishiki' | 2019 | 20.0 | 3.7 | 4.0 | 3.3 |
| | 2020 | 19.4 | 4.3 | 2.3 | 2.0 |
| | 2021 | 21.7 | 5.8 | 3.7 | 2.3 |
| | Avg. | 20.3 | 4.6 | 3.3 | 2.6 |

| Variety | Test Year | Maximum breaking stress (g) | Acidity (g/100 ml) | Sugar content (° Brix) | Sugar acid ratio |
|---|---|---|---|---|---|
| 'HC10' | 2019 | | 0.65 | 22.7 | 35.2 |
| | 2020 | | 0.68 | 21.2 | 31.2 |
| | 2021 | 80.8 | 0.66 | 21.6 | 32.6 |
| | Avg. | | 0.66 | 21.9 | 32.9 |
| 'Sato Nishiki' | 2019 | | 0.50 | 15.6 | 31.0 |
| | 2020 | | 0.42 | 14.6 | 34.8 |
| | 2021 | 69.5 | 0.57 | 18.1 | 31.6 |
| | Avg. | | 0.50 | 16.1 | 32.3 |

TABLE 24

| Fruit quality at prime of harvest (Yoichi Town) | | | | | |
|---|---|---|---|---|---|
| Line/ Variety' | Test Year | Fruit transverse diameter (mm) | Fruit size (g) | Skin coloration (1 weak to 5 strong) | Fruit firmness (1 soft to 5 firm) |
| 'HC10' | 2019 | 28.6 | 10.5 | 4.5 | 3.2 |
| | 2020 | 27.1 | 10.4 | 4.2 | 2.2 |
| | 2021 | 28.7 | 11.4 | 3.7 | 2.7 |
| | Avg. | 28.1 | 10.8 | 4.1 | 2.7 |
| 'Benishuho' | 2019 | 26.4 | 7.6 | 4.7 | 4.0 |
| | 2020 | 26.9 | 9.8 | 3.5 | 3.8 |
| | 2021 | 26.8 | 9.3 | 3.5 | 3.8 |
| | Avg. | 26.7 | 8.9 | 3.9 | 3.9 |

TABLE 24-continued

| Fruit quality at prime of harvest (Yoichi Town) | | | | | |
|---|---|---|---|---|---|
| 'Sato Nishiki' | 2019 | 23.4 | 5.7 | 5.0 | 2.0 |
| | 2020 | 21.8 | 5.7 | 3.0 | 2.0 |
| | 2021 | 22.3 | 6.2 | 4.0 | 1.5 |
| | Avg. | 22.5 | 5.9 | 4.0 | 1.8 |
| Line/ Variety' | Test Year | Maximum breaking stress (g) | Acidity (g/100 ml) | Sugar content (° Brix) | Sugar acid ratio |
| 'HC10' | 2019 | | 0.56 | 22.9 | 40.5 |
| | 2020 | | 0.48 | 18.5 | 38.8 |
| | 2021 | 72.6 | 0.50 | 19.5 | 38.8 |
| | Avg. | | 0.51 | 20.3 | 39.4 |
| 'Benishuho' | 2019 | | 0.68 | 23.9 | 35.2 |
| | 2020 | | 0.52 | 23.0 | 44.3 |
| | 2021 | 90.9 | 0.50 | 22.6 | 45.1 |
| | Avg. | | 0.57 | 23.2 | 40.9 |
| 'Sato Nishiki' | 2019 | | 0.65 | 22.2 | 33.9 |
| | 2020 | | 0.55 | 18.5 | 33.7 |
| | 2021 | 77.9 | 0.59 | 20.3 | 34.3 |
| | Avg. | | 0.60 | 20.3 | 34.0 |

The incidence of cold damage, frost damage, and disease and pestilence was also determined. There was no incidence of cold damage during test period. According to the results of Fukagawa City and Mashike Town, Japan, the frost damage was more than that of 'Sato Nishiki' and equivalent to or less than 'Nanyo' and 'Benishuho'.

The chilling requirement for 'Himari' is considered to be 7.2° C., 1440 hours.

'Himari' offers a combination of improved properties.

Cherry is one of the main products of fruit trees in Hokkaido, Japan. The main cultivated varieties in Hokkaido, Japan are 'Hokko' (unpatented), medium-maturing and with strong cold hardiness, and 'Nanyo', late-maturing and large in size, in addition to medium-maturing 'Sato Nishiki', which occupies about 50% of the cultivated area. Although each of these varieties has excellent characteristics, there are many points to be improved. Among them, 'Nanyo' and 'Sato Nishiki' are cross-incompatible because they have the same S genotype, and they are unstable factors of fruit production because they do not function as pollinating trees. 'Nanyo' has problems in the quality of fruit, such as difficulty in skin coloration and inferior transportability due to soft flesh.

'Himari' is a late-maturing plant which is harvested in mid-to late-July in Hokkaido, Japan. Compared to 'Nanyo', 'Himari' fruit has a large size, good skin coloration, firm flesh, and excellent eating quality. The main use is eating as fresh food. Fruit retains its edible quality when stored under refrigerated conditions for about a week. The S genotype is $S_1S_3$, which is cross-compatible with most cultivated varieties including 'Sato Nishiki'. Therefore, 'HC10' can improve the pollination environment of orchards and contribute to ensuring the fruiting of other varieties.

As described above, by replacing 'HC10' with most of 'Nanyo' and spreading the use of 'HC10', it is possible to improve the quality of Hokkaido, Japan-made cherries, contribute to the stable production of 'Sato Nishiki', which is a basic variety as a pollination tree, and contribute to the promotion of cherry cultivation in Hokkaido by contributing to the diversification of products not only in market shipment but also in tourist fruit farms and direct sales depots.

What is claimed is:

1. A new and distinct variety of cherry tree having the characteristics substantially as described and illustrated herein.

* * * * *